(12) United States Patent
Watanabe et al.

(10) Patent No.: US 8,481,735 B2
(45) Date of Patent: Jul. 9, 2013

(54) ORGANIC METAL COMPLEX AND PROCESS FOR PREPARING AMINE COMPOUND

(75) Inventors: Masahito Watanabe, Saitama (JP); Junichi Hori, Saitama (JP); Kunihiko Murata, Saitama (JP)

(73) Assignee: Kanto Kagaku Kabushiki Kaisha, Tokyo (JP)

( * ) Notice: Subject to any disclaimer, the term of this patent is extended or adjusted under 35 U.S.C. 154(b) by 285 days.

(21) Appl. No.: 12/722,819

(22) Filed: Mar. 12, 2010

(65) Prior Publication Data

US 2010/0234596 A1 Sep. 16, 2010

(30) Foreign Application Priority Data

Mar. 12, 2009 (JP) ................................. 2009-060179

(51) Int. Cl.
*C07F 15/00* (2006.01)
*B01J 31/12* (2006.01)

(52) U.S. Cl.
USPC ............................. 546/10; 502/166; 502/167

(58) Field of Classification Search
USPC .................................... 546/10; 502/166, 167
See application file for complete search history.

(56) References Cited

U.S. PATENT DOCUMENTS

2004/0267051 A1 12/2004 Boerner et al.

FOREIGN PATENT DOCUMENTS

| EP | 2 172 443 A1 | 4/2010 |
| JP | 2004-537588 A | 12/2004 |
| JP | 4059978 B2 | 12/2007 |
| WO | WO 02 10101 A1 | 2/2002 |
| WO | WO 2009/005024 A1 | 1/2009 |

OTHER PUBLICATIONS

Camm, K.D. et al., "Synthesis, molecular structure and evaluation of new organometallic ruthenium anticancer agents," *Dalton Transactions* Nov. 16, 2009; 10914-10925.

Gemel, C. et al., "Synthesis and characterization of ruthenium quinolin-8-olate complexes. Unexpected formation of a $k^1$-hydrotris(pyrazolyl)borate complex," *J. Chem. Soc., Dalton Trans.* 2000; 2607-2612.

Thai, T-T. et al., "Pentamethylcyclopentadienyl rhodium and iridium complexes containing oxinato ligands," *Inorganic Chemistry Communications* Jun. 21, 2009; 12:806-807.

Thai, T-T. et al., "Arene ruthenium oxinato complexes: Synthesis, molecular structure and catalytic activity for the hydrogenation of carbon dioxide in aqueous solution," *Journal of Organometallic Chemistry* Sep. 12, 2009; 694:3973-3981.

Van Rijt, S.H. et al., "Amide Linkage Isomerism As an Activity Switch for Organometallic Osmium and Ruthenium Anticancer Complexes," *J. Med. Chem.* Sep. 30, 2009; 52:7753-7764.

Gross, T. et al., "Synthesis of Primary Amines: First Homogeneously Catalyzed Reductive Amination and Ammonia," *Organic Letters* 2002; 4(12):2055-2058.

Kitamura, M. et al., "Catalytic Leuckart-Wallach-Type Reductive Amination of Ketones," *J. Org. Chem.* 2002; 67:8685-8687.

Tararov, V. I. et al., "On the reductive amination of aldehydes and ketones catalyzed by homogeneous Rh(I) complexes," *Chem. Commun.* 2000; 1867-1868.

*Primary Examiner* — Charanjit Aulakh
(74) *Attorney, Agent, or Firm* — Wolf, Greenfield & Sacks, P.C.

(57) ABSTRACT

[Problem]
The present invention aims to provide a novel organometallic compound that can be used as a general-use highly active catalyst with superior selectivity for functional groups.
[Means for Solving Problem]
The present invention relates to an organometallic compound having a novel specific structure of general formula (1):

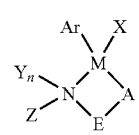

(1)

and to a general-use highly active catalyst used in reductive amination reaction with superior selectivity for functional groups that comprises said organometallic compound, and to a process for preparing amine compounds by reductive amination reaction using said catalyst.

9 Claims, 1 Drawing Sheet

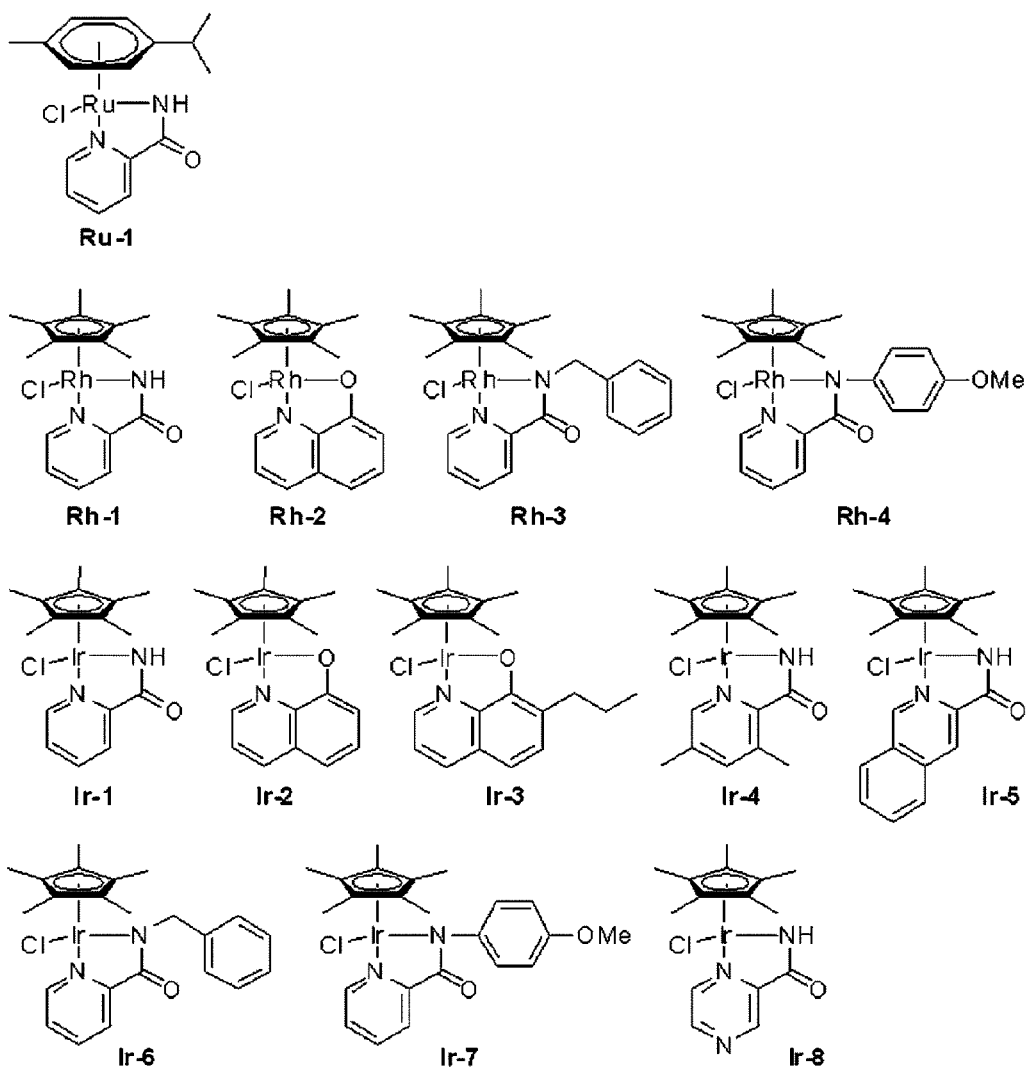

ORGANIC METAL COMPLEX AND PROCESS FOR PREPARING AMINE COMPOUND

TECHNICAL FIELD

The present invention relates to a novel organometallic complex. The present invention also relates to a catalyst with superior practical utility comprising said organometallic complex. Furthermore, the present invention relates to a use of said catalyst in reductive amination reaction.

BACKGROUND ART

A process for preparing an amine compound by means of reaction of ammonia or a primary or secondary amine compound with a carbonyl compound has been known as a reductive amination reaction, which is one of the standard processes for preparing amine compounds. As preparation processes of amine compounds by means of reductive amination reaction, the following processes have been conventionally known: 1) a method by a hydrogenation reaction using solid catalysts such as Raney Ni, Raney Co, Pt/activated carbon, and Pd/activated carbon as a heterogeneous catalyst, 2) a method wherein a boron reactant such as $NaBH_3CN$ or $NaBH(OAc)_3$ is used as a hydride reducing agent, and 3) a method wherein a metal complex catalyst is used as a homogeneous catalyst. The method of 1) is described in, for example, J. Am. Chem. Soc. 1941, 63, 749 and J. Org. Chem. 1962, 27, 2205.

Regarding the method of 2), the following methods have been known: a) a method using $NaBH_3CN$ described in J. Am. Chem. Soc. 1971, 93, 2897, b) a method using $NaBH(OAc)_3$ described in J. Org. Chem. 1996, 61, 3849, c) a method using pyridine borane described in J. Org. Chem. 1995, 60, 5995, d) a method using 2-picoline borane descried in JP2004256511 (2004), and e) a method using 5-ethyl-2-methylpyridine borane described in Tetrahedron Letters 2008, 49, 5152-5155.

Regarding the method of 3), the following methods have been known: in Patent Literature 1, a method for preparing a primary amine by reaction of a carbonyl compound, ammonia and hydrogen under the presence of a hydrogenation catalyst; in Non-patent Literature 1, a method by means of hydrogenation reaction using a rhodium complex having a phosphine ligand; in Non-patent Literature 2, a method by means of hydrogenation reaction using a combination of a [Rh(cod)Cl]$_2$ complex and a TPPTS ligand; in Non-patent Literature 3, a method using [Cp*RhCl$_2$]$_2$ as a complex catalyst wherein ammonium formate is used as an amine source and a hydrogen source; in Patent Literature 2, a method by means of reductive hydride-transfer animation of a carbonyl compound with an amine compound under the presence of a hydrogen donator as a reducing agent and a transition-metal complex catalyst comprising at least one metal selected from the group consisting of Ru, Rh, Ir.

However, the preparation processes by means of hydrogenation reaction using solid catalysts have problems in terms of safety and operability of reaction, because they require a pressure-resistant reactor due to the use of hydrogen gas as a hydrogen source, and also the processes cannot be applied to substrates having carbon-carbon multiple bonds and functional groups such as cyano group and nitro group that are apt to be hydrogenated. Since boron reactants do not require a pressure-resistant reactor, they will make a method with superior operability; however, because it is not a catalyst reaction, the method is inferior from the viewpoints of economical and environmental aspects. In addition, the following problems exist for each reactant.

The method using $NaBH_3CN$ has a difficulty in industrial utilization due to its toxicity. The method using $NaBH(OAc)_3$ has a limitation in solvents used due to its solubility, and an excessive amount of $NaBH(OAc)_3$ must be used because there is only one hydride source in its molecule. Regarding the method using pyridine borane, the storage stability of the reagent itself is poor, and has a problem that it decomposes at 54° C. or more. The method using 2-picoline borane has a problem of handling because its melting point is 44-45° C., although the stability of the reactant is higher than that of pyridine borane. 5-ethyl-2-methylpyridine borane has a problem that the reactant is difficult to be removed from a reaction liquid, similar to the above two pyridine-borane reactants.

As an example wherein a homogeneous catalyst is used, a method described in JP No. 4059978 requires an pressure-resistant reactor because it uses hydrogen as a hydrogen source, and reaction is performed under high-temperature (150° C.) and high-pressure (50 atm or more) conditions; therefore the method has problems in industrial application in terms of safety and reaction operability. A method described in Chem. Comm., 2000, 1867-1868 is a reaction under high-pressure condition (50 atm), and it generates alcohols as a by-product and has deteriorated selectivity of amines. Thus, the method cannot be an efficient preparation process of amine compounds. A method described in Org. Lett. 2002, 4, 2055-2058, that is, a hydrogenation reaction of combination of a [Rh(cod)Cl]$_2$ complex and a TPPTS ligand, is performed under high temperature and high pressure conditions; therefore, its industrial application has difficulties in terms of safety and reaction operability.

As shown in J. Org. Chem. 2002, 67, 8685-8687, a method wherein [Cp*RhCl$_2$]$_2$ complex as an organometallic complex is used as a catalyst is superior in terms of reaction operability and safety, because it uses solid ammonium formate as a hydrogen source and amine source. However, because catalyst activity is low, its industrial application may be problematic. JP A, 2004-537588 describes a method that has difficulties in industrial application due to its low reaction efficiency, such as a [substrate/catalyst] ratio of approximately 50-100, and the generation of by-product alcohols and a possibility of incomplete reaction.

Under these circumstances, a novel preparation method of amine compounds by means of reductive amination reaction, using a catalyst for general use having high activity and superior functional-group selectivity, has been conventionally desired.

[Citation List]

[Patent Literature 1] JP, B, 4059978

[Patent Literature 1] JP, A, 2004-537588

[Non Patent Literature 1] Tararov, V. I. et al., J., Chem. Comm., 2000, 1867-1868.

[Non Patent Literature 2] Gross, T. et al., Org. Lett. 2002, 4, 2055-2058.

[Non Patent Literature 3] Kitamura, M. et al., J. Org. Chem. 2002, 67, 8685-8687.

SUMMARY OF INVENTION

Technical Problem

An object of the present invention is to provide a novel organometallic compound that can be used as a catalyst for general use having high activity and superior functional-group selectivity.

Solution to Problem

The present inventors have extensively investigated complexes having a catalyst activity in reductive amination reaction of carbonyl compound and amine compound, and found that ruthenium, rhodium and iridium complexes having a nitrogen-containing ligand are superior organometallic compounds in reductive amination reaction; thus the present invention has been accomplished.

Namely, the present invention relates to an organometallic compound of general formula (1):

[Chem. 1]

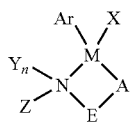

(1)

(wherein in general formula (1), Ar is a cyclopentadienyl group or an aromatic compound in which one or more hydrogen atoms may be substituted by a substituent W, W denotes a saturated or unsaturated C1-10 hydrocarbon group, an aryl group, a heterocyclyl group, an alkoxy group, a fluoroalkyl group, an acyl group, an ester group, a hydroxyl group, an amino group, an amide group, a carboxyl group, a sulfonyl group, a nitro group, a cyano group, a sulfenyl group, a sulfo group, a thiol group, a silyl group or a halogen group, M is ruthenium, rhodium, or iridium, X is a hydride group or an anionic group, E denotes a link group which is a saturated or unsaturated C1-6 hydrocarbon group in which one or more hydrogen atoms may be substituted by a substituent W, or which is an arylene group in which one or more hydrogen atoms may be substituted by C1-10 alkyl group, cycloalkyl group, aryl group, alkenyl group, acyl group, halogen group, ester group, amino group, amide group, carboxyl group, hydroxyl group, nitro group, cyano group, sulfenyl group, sulfo group, or thiol group (wherein one or more hydrogen atoms in said substituents may further be substituted by W), A is an amide group having a binding mode of "M-NR$^1$C(O)-E," a thioamide group having a binding mode of "M-NR$^1$C(S)-E," or an oxygen atom, wherein when A is an oxygen atom, E is an arylene group in which one or more hydrogen atoms may be substituted by a substituent W, R$^1$ denotes a hydrogen atom, a C1-10 alkyl group, a cycloalkyl group, an aryl group, a heterocyclyl group, an alkenyl group, an alkynyl group, an ester group, an acyl group, a sulfinyl group, a sulfonyl group or a silyl group, in which one or more hydrogen atoms may be substituted by a substituent W (wherein one or more hydrogen atoms in said substituent W may further be substituted by W), Y and Z are the same or different each other, and denote a C1-10 alkyl group, a cycloalkyl group, a heterocyclyl group, a silyl group, an aryl group, or an alkenyl group, in which one or more hydrogen atoms may be substituted by a substituent W, wherein "Y and Z," "Z and E," "Y and E," or "Y and Z and E" may be bound to form a ring, and n denotes an integer of 0 or 1, wherein when n=0, the bond between N—Z or N-E is a double bond), provided that those in which Yn-N(Z)-E comprises an azetidine ring, and those in which M is ruthenium and a ligand A-E-N(Y) (Z) is a 8-quinolinolate group are excluded.

The present invention also relates to the above organometallic compound, characterized in that a part of formula (1) expressed by general formula (2) below:

[Chem. 2]

(2)

is a group comprising a nitrogen-containing six-membered aromatic ring structure.

In addition, the present invention relates to the above organometallic compound, characterized in that the organometallic compound of formula (1) is either a compound of general formula (3):

[Chem. 3]

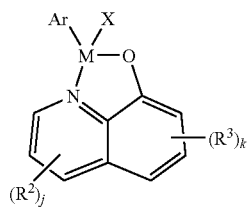

(3)

(wherein in general formula (3), Ar, M and X have the same meanings as described above, R$^2$ and R$^3$ are mutually identical or mutually different, and denote a hydrogen atom, a halogen atom, a nitro group, a cyano group, a hydroxyl group, a sulfo group, a thiol group, a carboxyl group, or the following groups in which one or more hydrogen atoms may be substituted by a substituent W: a C1-10 alkyl group, a cycloalkyl group, an aryl group, a heterocyclyl group, an alkenyl group, an alkynyl group, an alkoxy group, an ester group, a fluoroalkyl group, an acyl group, a sulfonyl group, an amino group, an amide group, an sulfenyl group, or a silyl group, W has the same meaning as described above, j and k are, independently of one another, an integer from 0 to 3, wherein one or more of carbon atoms, which is (are) not bonded to R$^2$ or R$^3$, in the quinoline ring structure may be replaced with a nitrogen atom, and wherein when j and/or k is (are) 2 or more, 2 or more of R$^2$ and/or R$^3$ may be linked each other to form (a) ring(s)), or a compound of general formula (4):

[Chem. 4]

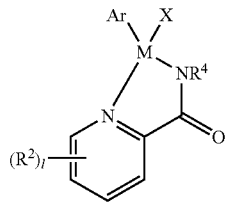

(4)

(wherein in general formula (4), Ar, M and X have the same meanings as described above, R$^2$ has the same meaning as the above R$^2$ and R$^3$, R$^4$ denotes a hydrogen atom, a C1-10 alkyl group, an cycloalkyl group, an aryl group, a heterocyclyl group, an alkenyl group, an alkynyl group, an ester group, an acyl group, a sulfinyl group, a sulfonyl group, or a silyl group, in which one or more hydrogen atoms may be substituted by a substituent W, W has the same meaning as described above, l denotes an integer from 0 to 4, wherein one or more of carbon atoms, which is (are) not bonded to $R^2$, in the pyridine ring structure may be replaced with a nitrogen atom, and wherein when l is 2 or more, 2 or more of $R^2$ may be linked each other to form (a) ring(s)).

Furthermore, the present invention relates to a catalyst used for reductive amination reaction, comprising at least one organometallic compound of general formula (5):

[Chem. 5]

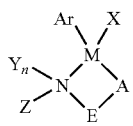
(5)

(wherein in general formula (5), Ar is a cyclopentadienyl group or an aromatic compound in which one or more hydrogen atoms may be substituted by a substituent W, W denotes a saturated or unsaturated C1-10 hydrocarbon group, an aryl group, a heterocyclyl group, an alkoxy group, a fluoroalkyl group, an acyl group, an ester group, a hydroxyl group, an amino group, an amide group, a carboxyl group, a sulfonyl group, a nitro group, a cyano group, a sulfenyl group, a sulfo group, a thiol group, a silyl group or a halogen group, M is ruthenium, rhodium, or iridium, X is a hydride group or an anionic group, E denotes a link group which is a saturated or unsaturated C1-6 hydrocarbon group in which one or more hydrogen atoms may be substituted by a substituent W, or which is an arylene group wherein one or more hydrogen atoms may be substituted by C1-10 alkyl group, cycloalkyl group, aryl group, alkenyl group, acyl group, halogen group, ester group, amino group, an amide group, a carboxyl group, a hydroxyl group, nitro group, cyano group, sulfenyl group, sulfo group, or thiol group (wherein one or more hydrogen atoms in said substituents may further be substituted by W), A is an amide group having a binding mode of "M-NR$^1$C(O)-E," a thioamide group having a binding mode of "M-NR$^1$C(S)-E," or an oxygen atom, wherein when A is an oxygen atom, E is an arylene group in which one or more hydrogen atoms may be substituted by a substituent W, $R^1$ denotes a hydrogen atom, a C1-10 alkyl group, a cycloalkyl group, an aryl group, a heterocyclyl group, an alkenyl group, an alkynyl group, an ester group, an acyl group, a sulfinyl group, a sulfonyl group or a silyl group, in which one or more hydrogen atoms may be substituted by a substituent W (wherein one or more hydrogen atoms in said substituent W may further be substituted by W), Y and Z are the same or different each other, and denote a C1-10 alkyl group, a cycloalkyl group, an aryl group, a heterocyclyl group, an alkenyl group, or a silyl group, in which one or more hydrogen atoms may be substituted by a substituent W, wherein "Y and Z," "Z and E," "Y and E," or "Y and Z and E" may be bound to form a ring, and n denotes an integer of 0 or 1, wherein when n=0, the bond between N—Z or N-E is a double bond).

In addition, the present invention relates to the above catalyst, characterized in that a part of formula (5) expressed by general formula (6) below:

[Chem. 6]

(6)

(wherein in general formula (6), n=0 and, N, E and Z have the same meanings as described above) is a group comprising a nitrogen-containing aromatic ring structure.

Furthermore, the present invention relates to the above catalyst, characterized in that M in formula (5) is rhodium or iridium.

In addition, the present invention relates to a process for preparing an amine compound, characterized in that the amine compound is prepared by reacting a hydrogen-donating organic or inorganic compound with an imine compound or an enamine compound under the presence of the above catalyst.

The present invention also relates to the above process for preparing the amine compound, characterized in that the amine compound is prepared by the reaction of an imine compound or an enamine compound generated by mixing a carbonyl compound with an amine compound in a reaction system.

In addition, the present invention relates to a process for preparing an amine compound, characterized in that a carbonyl compound, an amine compound and a hydrogen-donating organic or inorganic compound are reacted under the presence of an organometallic compound of general formula (7):

[Chem. 7]

(wherein in general formula (7), Ar, M and X have the same meanings as described above, and m denotes an integer of 2 or greater) and an organic compound of general formula (8):

[Chem. 8]

(8)

(wherein in general formula (8), A, E, Y, Z and n have the same meanings as described above).

Furthermore, the present invention relates to the above process for preparing an amine compound, wherein the hydrogen-donating organic or inorganic compound is formic acid or formate.

ADVANTAGEOUS EFFECTS OF INVENTION

With the present invention, a catalyst with superior practical utility for preparation processes of amine compounds by means of reductive amination reaction of carbonyl compound and amine compound can be provided, so that amine compounds can be produced highly efficiently.

BRIEF DESCRIPTION OF DRAWINGS

FIG. 1 shows representative organometallic compounds of the present invention.

DESCRIPTION OF EMBODIMENTS

Hereinafter, the present invention will be described in detail.

In a nitrogen-containing organometallic complex of the present invention, Ar in general formula (1):

[Chem. 9]

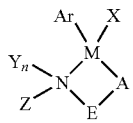

(1)

is, typically, a cyclopentadienyl group or an aromatic compound in which one or more hydrogen atoms may be substituted; specific examples of Ar include, but are not limited to, unsubstituted benzene, benzene having an alkyl group, such as toluene, o-, m- and p-xylene, o-, m- and p-cymene, 1,2,3-, 1,2,4- and 1,3,5-trimethylbenzene, 1,2,4,5-tetramethylbenzene, 1,2,3,4-tetramethylbenzene, pentamethylbenzene, and hexamethylbenzene; benzene having an unsaturated hydrocarbon group, such as benzyl, vinyl, and allyl; benzene having heteroatoms, such as hydroxyl group, alkoxy group, ester group, and amino group. The number of substituents in a benzene ring is any number from 1 to 6, and substituents may be at any positions. From the viewpoint of easiness in the synthesis of complex, Ar is preferably p-cymene and 1,3,5-trimethylbenzene.

Examples of cyclopentadienyl group that may have a substituent include, but are not limited to, cyclopentadienyl group, methylcyclopentadienyl group, ethylcyclopentadienyl group, isopropylcyclopentadienyl group, phenylcyclopentadienyl group, benzylcyclopentadienyl group, 1,2-dimethylcyclopentadienyl group, 1,3-dimethylcyclopentadienyl group, 1,2,3-trimethylcyclopentadienyl group, 1,2,4-trimethylcyclopentadienyl group, 1,2,3,4-tetramethylcyclopentadienyl group, and 1,2,3,4,5-pentamethylcyclopentadienyl group (Cp*). From the viewpoint of easiness in the synthesis of complex, it is preferably a 1,2,3,4,5-pentamethylcyclopentadienyl group (Cp*).

The substituent W is, typically, a saturated or unsaturated C1-10 hydrocarbon group, aryl group, heterocyclyl group, alkoxy group, fluoroalkyl group, acyl group, ester group, hydroxyl group, amino group, amide group, carboxyl group, sulfonyl group, nitro group, cyano group, sulfenyl group, sulfo group, thiol group, silyl group or halogen group; in particular, it is a saturated or unsaturated C1-10 hydrocarbon group, aryl group, heterocyclyl group, alkoxy group, acyl group, ester group, hydroxyl group, amino group, sulfonyl group, silyl group or halogen group.

Specific examples of W include, but are not limited to, methyl group, ethyl group, n-propyl group, i-propyl group, butyl group, pentyl group, hexyl group, cyclohexylene group, ethenyl group, propenyl group, butenyl group, phenyl group, toluoyl group, naphthyl group, pyridyl group, furanyl group, methoxy group, ethoxy group, propoxy group, acetyl group, propanoyl group, cyclohexanecarbonyl group, benzoyl group, methoxycarbonyl group, ethoxycarbonyl group, hydroxyl group, methylamino group, ethylamino group, dimethylamino group, methylsulfonyl group, ethylsulfonyl group, methylsilyl group, dimethylsilyl group, fluoro group, chloro group, and trifluoromethyl group. From the viewpoint of easiness in the synthesis of complex, it is preferably a saturated or unsaturated hydrocarbon group, and more preferably a methyl group or i-propyl group.

M in general formula (1) is either ruthenium, rhodium or iridium. From the viewpoint of high level of catalyst activity, it is preferably rhodium or iridium.

X in general formula (1) is, typically, a hydride group or anionic group. Specific examples of X include, but are not limited to, hydride group, hydroxy group, alkoxy group, cross-linked oxo group, fluorine group, chlorine group, bromine group, iodine group, tetrafluoroborate group, tetrahydroborate group, tetrakis pentafluorophenyl borate group, tatrakis[3',5'-bis(trifluoromethyl)phenyl]borate group, hexafluorophosphate group, hexafluoroantimonate group, hexachloroantimonate group, hexafluoroarsenate group, perchlorate group, acetoxy group, benzoyloxy group, (2',6'-dihydroxybenzoyl)oxy group, (2',5'-dihydroxybenzoyl)oxy group, (3'-aminobenzoyl)oxy group, (2',6'-dimethoxybenzoyl)oxy group, (2',4',6'-triisopropylbenzoyl)oxy group, 1-naphthalenecarboxylic acid group, 2-naphthalenecarboxylic acid group, trifluoroacetoxy group, trifluoromethanesulfonimide group, nitromethyl group, nitroethyl group, toluenesulfonate group, methanesulfonate group, ethanesulfonate group, n-propanesulfonate group, isopropanesulfonate group, n-butanesulfonate group, fluorosulfonate group, fluoromethanesulfonate group, difluoromethanesulfonate group, trifluoromethanesulfonate group, and pentafluoroethanesulfonate group. From the viewpoint of easiness in the synthesis of complex, it is preferably a chlorine group, bromine group and iodine group.

The link group E is typically a saturated or unsaturated C1-6 hydrocarbon group or an arylene group in which one or more hydrogen atoms may be substituted. Specific examples of E include, but are not limited to, methylene group, ethylene group, propylene group, cyclohexylene group, vinylene group, propynylene group, butenylene group, phenylene group, and naphthalenylene group. From the viewpoints of high catalyst activity and easiness in the synthesis of complex, it is preferably a methylene group, ethylene group, phenylene group, and naphthalenylene group, and more preferably a methylene group and phenylene group.

When E is an arylene group, examples of the substituents for one or more hydrogen atoms typically include C1-10 alkyl group, cycloalkyl group, aryl group, alkenyl group, acyl group, halogen group, ester group, amino group, amide group, carboxyl group, hydroxyl group, nitro group, cyano group, sulfenyl group, sulfo group, or thiol group, and in particular, C1-10 alkyl group, cycloalkyl group, aryl group, alkenyl group, or acyl group. One or more hydrogen atoms in these substituents may further be substituted by a substituent W.

A in general formula (1) is an amide group having a binding mode of "M-NR$^1$C(O)-E," a thioamide group having a binding mode of "M-NR$^1$C(S)-E," or an oxygen atom. R$^1$ is typically a hydrogen atom, a C1-10 alkyl group, a cycloalkyl group, an aryl group, a heterocyclyl group, an alkenyl group, an alkynyl group, an ester group, an acyl group, a sulfinyl group, a sulfonyl group or a silyl group, in which one or more hydrogen atoms may be substituted by a substituent W. One or more hydrogen atoms of the substituent W in these substituents may further be substituted by a substituent W.

Specific examples of R$^1$ include, but are not limited to, hydrogen atom, methyl group, ethyl group, isopropyl group, tert-butyl group, isobutyl group, benzyl group, cyclohexyl group, phenyl group, pyridyl group, vinyl group, ethynyl group, group having an ester bond, acetyl group, methylsulfonyl group, ethylsulfonyl group, methylsilyl group, and dimethylsilyl group. From the viewpoint of high catalyst activity and high yield in reaction, it is preferably a hydrogen atom, methyl group, isopropyl group, tert-butyl group, isobutyl group, benzyl group, phenyl group, or 4-methoxyphenyl group. When A is an oxygen atom, E is limited to an arylene group wherein one or more hydrogen atoms may be substituted by a substituent W.

Y and Z in general formula (1) are, typically and independently of one another, a C1-10 alkyl group, a cycloalkyl group, a heterocyclyl group, a silyl group, an aryl group, or an alkenyl group, in which one or more hydrogen atoms may be substituted by a substituent W. Specific examples of Y and Z include, but are not limited to, methyl group, ethyl group, cyclohexyl group, phenyl group, and vinyl group. From the viewpoint of easiness in the synthesis of complex, they are preferably a methyl group or an ethyl group. Y, Z and E may be mutually bound to form a ring. Specific examples include, but are not limited to, cases wherein Z and E are bound to form a piperidyl group or pyridyl group. When n denotes 0, N—Z or N-E is a double bond.

The structure of the part of formula (1), which is expressed by general formula (2) below:

[Chem. 10]

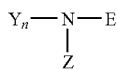

(2)

is preferably a group comprising a nitrogen-containing six-membered aromatic ring structure, from the viewpoint of high catalyst activity. In this case, n is 0, and N in general formula (2) is a hetero nitrogen atom in the nitrogen-containing six-membered aromatic ring structure, so that Z and E are bound to form a ring structure. This part may be any structure comprising a nitrogen-containing six-membered aromatic ring structure, for example, not only a nitrogen-containing six-membered monocyclic aromatic ring such as a pyridine ring, a pyridazine ring, a pyrazine ring, a Pyrimidine ring, or a triazine ring but also a polycyclic aromatic ring, which containing a nitrogen-containing six-membered aromatic ring structure, such as a quinoline ring, an isoquinoline ring, a quinazoline ring, a quinoxaline ring, acridine ring, a cinnoline ring, or a phthalazine ring.

From the viewpoint of high catalyst activity, it is preferably a compound of general formula (3):

[Chem. 11]

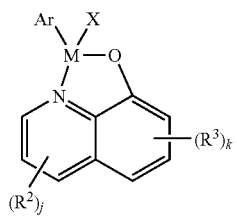

(3)

In this formula, $R^2$ and $R^3$ are, typically and independently of one another, a hydrogen atom, a halogen atom, or a C1-10 alkyl group, an cycloalkyl group, an aryl group, a heterocyclyl group, an alkenyl group, an alkynyl group, an alkoxy group, an ester group, a fluoroalkyl group, an acyl group, a sulfonyl group, a nitro group, a cyano group, a hydroxyl group, a sulfo group, a thiol group, an amino group, an amide group, a carboxyl group, a sulfenyl group, or a silyl group, in which one or more hydrogen atoms may be substituted by a substituent W; in particular, they are a hydrogen atom, a halogen atom, or a C1-10 alkyl group, an cycloalkyl group, an aryl group, a heterocyclyl group, an alkenyl group, an alkynyl group, an alkoxy group, an ester group, an acyl group, a sulfonyl group, a hydroxyl group, or a silyl group, in which one or more hydrogen atoms may be substituted by a substituent W. A plurality of $R^2$ and $R^3$ may be introduced, and the numbers of substitution j and k are, independently of one another, an integer from 0 to 3, wherein when j is 2 or more, 2 or more of $R^2$ may be linked each other to form (a) ring(s) such as phenanthridine ring, or acridine ring. Further, one or more of carbon atoms, which is (are) not bonded to $R^2$ or $R^3$, in the quinoline ring structure may be replaced with a nitrogen atom, for example, to form naphthyridine ring, quinoxaline ring, cinnoline ring, quinazoline ring, phthalazine ring, or the like.

Specific examples of $R^2$ and $R^3$ include, but are not limited to, methyl group, ethyl group, cyclohexyl group, phenyl group, pyridyl group, vinyl group, ethynyl group, group having an ester bond, acetyl group, methylsulfonyl group, ethylsulfonyl group, methylsilyl group, and dimethylsilyl group. From the viewpoint of high catalyst activity, they are preferably a methyl group, ethyl group or propyl group.

In addition, from the viewpoint of high catalyst activity, it is preferably a compound of general formula (4):

[Chem. 12]

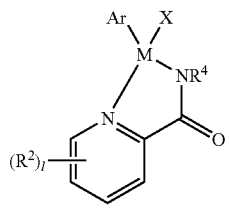

(4)

In this formula, $R^2$ has the same meaning as described above, and its number of substitution l is an integer from 0 to 4. $R^4$ is, typically, hydrogen atom, a C1-10 alkyl group, a cycloalkyl group, an aryl group, a heterocyclyl group, an alkenyl group, an alkynyl group, an ester group, an acyl group, a sulfinyl group, a sulfonyl group, or a silyl group, in which one or more hydrogen atoms may be substituted by a substituent W. Specific examples of $R^4$ include, but are not limited to, for example, hydrogen atom, methyl group, ethyl group, isopropyl group, tert-butyl group, isobutyl group, benzyl group, cyclohexyl group, phenyl group, pyridyl group, vinyl group, ethynyl group, group having an ester bond, acetyl group, sulfonyl group, and silyl group. From the viewpoint of high catalyst activity and high yield in reaction, it is preferably hydrogen atom, a methyl group, ethyl group, isopropyl group, tert-butyl group, benzyl group, phenyl group or 4-methoxyphenyl group. A plurality of $R^2$ may be introduced, and the number of substitution l denotes an integer from 0 to 4, wherein when l is 2 or more, 2 or more of $R^2$ may be linked each other to form (a) ring(s) such as quinoline ring, isoquinoline, or the like. Further, one or more of carbon atoms, which is(are) not bonded to $R^2$, in the pyridine ring structure may be replaced with a nitrogen atom, for example, to form pyridazine ring, pyrazine ring, pyrimidine ring, triazine ring or the like.

The present invention also includes a catalyst used for reductive amination reaction, that comprises at least one compound of general formula (5):

[Chem. 13]

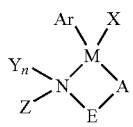

(5)

Ar is, typically, a cyclopentadienyl group or an aromatic compound in which one or more hydrogen atoms may be substituted; specific examples of Ar include, but are not limited to, unsubstituted benzene, benzene having an alkyl group, such as toluene, o-, m- and p-xylene, o-, m- and p-cymene, 1,2,3-, 1,2,4- and 1,3,5-trimethylbenzene, 1,2,4,5-tetramethylbenzene, 1,2,3,4-tetramethylbenzene, pentamethylbenzene, and hexamethylbenzene; benzene having an unsaturated hydrocarbon group, such as benzyl, vinyl, and allyl; benzene having heteroatoms, such as hydroxyl group, alkoxy group, ester group, and amino group. The number of substituents in a benzene ring is any number from 1 to 6, and substituents may be at any positions. From the viewpoint of easiness in the synthesis of complex, Ar is preferably p-cymene and 1,3,5-trimethylbenzene.

Examples of cyclopentadienyl group that may have a substituent include, but are not limited to, cyclopentadienyl group, methylcyclopentadienyl group, ethylcyclopentadienyl group, isopropylcyclopentadienyl group, phenylcyclopentadienyl group, benzylcyclopentadienyl group, 1,2-dimethylcyclopentadienyl group, 1,3-dimethylcyclopentadienyl group, 1,2,3-trimethylcyclopentadienyl group, 1,2,4-trimethylcyclopentadienyl group, 1,2,3,4-tetramethylcyclopentadienyl group, and 1,2,3,4,5-pentamethylcyclopentadienyl group (Cp*). From the viewpoint of easiness in the synthesis of complex, it is preferably a 1,2,3,4,5-pentamethylcyclopentadienyl group (Cp*).

The substituent W is, typically, a saturated or unsaturated C1-10 hydrocarbon group, aryl group, heterocyclyl group, alkoxy group, fluoroalkyl group, acyl group, ester group, hydroxyl group, amino group, amide group, carboxyl group, sulfonyl group, nitro group, cyano group, sulfenyl group, sulfo group, thiol group, silyl group or halogen group; in particular, it is a saturated or unsaturated C1-10 hydrocarbon group, aryl group, heterocyclyl group, alkoxy group, acyl group, ester group, hydroxyl group, amino group, sulfonyl group, silyl group or halogen group.

Specific examples of W include, but are not limited to, methyl group, ethyl group, n-propyl group, i-propyl group, butyl group, pentyl group, hexyl group, cyclohexylene group, ethenyl group, propenyl group, butenyl group, phenyl group, toluoyl group, naphthyl group, pyridyl group, furanyl group, methoxy group, ethoxy group, propoxy group, acetyl group, propanoyl group, cyclohexanecarbonyl group, benzoyl group, methoxycarbonyl group, ethoxycarbonyl group, hydroxyl group, methylamino group, ethylamino group, dimethylamino group, methylsulfonyl group, ethylsulfonyl group, methylsilyl group, dimethylsilyl group, fluoro group, chloro group, and trifluoromethyl group. From the viewpoint of easiness in the synthesis of complex, it is preferably a saturated or unsaturated hydrocarbon group, and more preferably a methyl group or i-propyl group.

M in general formula (5) is either ruthenium, rhodium or iridium. From the viewpoint of high level of catalyst activity, it is preferably rhodium or iridium.

X in general formula (5) is, typically, a hydride group or anionic group. Specific examples of X include, but are not limited to, hydride group, hydroxy group, alkoxy group, cross-linked oxo group, fluorine group, chlorine group, bromine group, iodine group, tetrafluoroborate group, tetrahydroborate group, tetrakis pentafluorophenyl borate group, tatrakis[3',5'-bis(trifluoromethyl)phenyl]borate group, hexafluorophosphate group, hexafluoroantimonate group, hexachloroantimonate group, hexafluoroarsenate group, perchlorate group, acetoxy group, benzoyloxy group, (2',6'-dihydroxybenzoyl)oxy group, (2',5'-dihydroxybenzoyl)oxy group, (3'-aminobenzoyl)oxy group, (2',6'-dimethoxybenzoyl)oxy group, (2',4',6'-triisopropylbenzoyl)oxy group, 1-naphthalenecarboxylic acid group, 2-naphthalenecarboxylic acid group, trifluoroacetoxy group, trifluoromethanesulfonimide group, nitromethyl group, nitroethyl group, toluenesulfonate group, methanesulfonate group, ethanesulfonate group, n-propanesulfonate group, isopropanesulfonate group, n-butanesulfonate group, fluorosulfonate group, fluoromethanesulfonate group, difluoromethanesulfonate group, trifluoromethanesulfonate group, and pentafluoroethanesulfonate group. From the viewpoint of easiness in the synthesis of complex, it is preferably a chlorine group, bromine group and iodine group.

The link group E is typically a saturated or unsaturated C1-6 hydrocarbon group or an arylene group, in which one or more hydrogen atoms may be substituted. Specific examples of E include, but are not limited to, methylene group, ethylene group, propylene group, cyclohexylene group, vinylene group, propynylene group, butenylene group, phenylene group, and naphthalenylene group. From the viewpoints of high catalyst activity and easiness in the synthesis of complex, it is preferably methylene group, ethylene group, phenylene group, and naphthalenylene group, and more preferably a methylene group and phenylene group.

When E is an arylene group, examples of the substituents for one or more hydrogen atoms typically include C1-10 alkyl group, cycloalkyl group, aryl group, alkenyl group, acyl group, halogen group, ester group, amino group, amide group, carboxyl group, hydroxyl group, nitro group, cyano group, sulfenyl group, sulfo group and thiol group, and in particular, C1-10 alkyl group, cycloalkyl group, aryl group, alkenyl group, and acyl group. One or more hydrogen atoms in these substituents may further be substituted by a substituent W.

A in general formula (5) is an amide group having a binding mode of "M-NR$^1$C(O)-E," a thioamide group having a binding mode of "M-NR$^1$C(S)-E," or an oxygen atom. R$^1$ is typically a hydrogen atom, a C1-10 alkyl group, a cycloalkyl group, an aryl group, a heterocyclyl group, an alkenyl group, an alkynyl group, an ester group, an acyl group, a sulfinyl group, a sulfonyl group or a silyl group, in which one or more hydrogen atoms may be substituted by a substituent W. One or more hydrogen atoms of the substituent W in these substituents may further be substituted by a substituent W.

Specific examples of R$^1$ include, but are not limited to, hydrogen atom, methyl group, ethyl group, isopropyl group, tert-butyl group, isobutyl group, benzyl group, cyclohexyl group, phenyl group, pyridyl group, vinyl group, ethynyl group, group having an ester bond, acetyl group, methylsulfonyl group, ethylsulfonyl group, methylsilyl group, and dimethylsilyl group. From the viewpoint of high catalyst activity and high yield in reaction, it is preferably a hydrogen atom, a methyl group, isopropyl group, tert-butyl group, isobutyl group, benzyl group, phenyl group or 4-methoxyphenyl group. When A is an oxygen atom, E is limited to an arylene group wherein one or more hydrogen atoms may be substituted by a substituent W.

Y and Z in general formula (5) are, typically and independently of one another, an alkyl group, a cycloalkyl group, a heterocyclyl group, a silyl group, an aryl group, a heterocyclyl group, an alkenyl group, or a silyl group. Specific examples of Y and Z include, but are not limited to, for example, methyl group, ethyl group, cyclohexyl group, phenyl group, pyridyl group, vinyl group, methylsilyl group, and dimethylsilyl group. From the viewpoint of easiness in the synthesis of complex, they are preferably a methyl group or ethyl group. Y, Z and E may be mutually bound to form a ring. Specific examples include, but are not limited to, cases wherein Z and E are bound to form a piperidyl group or pyridyl group. When n denotes 0, N—Z or N-E is a double bond.

The structure of the part of the catalyst of general formula (5) of the invention, wherein said structure is expressed by general formula (6) below:

[Chem. 14]

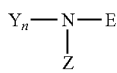

(6)

is preferably a group comprising a nitrogen-containing aromatic ring structure, from the viewpoint of high catalyst activity. In this case, n is 0, and N in general formula (6) is a hetero nitrogen atom in the nitrogen-containing aromatic ring structure, so that Z and E are bound to form a ring structure. Examples of the nitrogen-containing aromatic ring structure include, but are not limited to, pyridyl group and quinolyl group. Furthermore, any group comprising a nitrogen-containing aromatic ring structure may be used, for example, 5,6,7,8-tetrahydroquinolyl group.

Under the presence of the catalyst of the present invention, it is possible to produce amine compounds by reacting an imine compound or an enamine compound with a hydrogen-donating organic or inorganic compound.

The imine compound or enamine compound used in the invention may be easily obtained by, under the presence or absence of an acid catalyst, a condensation reaction of a carbonyl compound of general formula (9):

[Chem. 15]

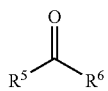

(9)

with an amine compound of general formula (10):
[Chem. 16]

NHR$^7$R$^8$  (10)

As an acid catalyst, addition of Bronsted acid or Lewis acid is desirable. Preferable examples of Bronsted acid include organic acid such as carboxylic acid, sulfonic acid, or phenols, or mineral acid such as phosphoric acid, boric acid, hydrochloric acid or nitric acid, and specific examples include, but are not limited to, Bronsted acid such as formic acid, acetic acid, p-toluenesulfonic acid, salicylic acid, chloroacetic acid, trifluoroacetic acid, phenol and binaphthol, or Lewis acid such as titanium tetraisopropoxide and aluminium triisopropoxide. These may be used alone, or a combination of a plurality of these may be used. In particular, since formic acid reacts also as a hydrogen donor, it is a preferable Bronsted acid for reductive amination reaction of carbonyl compound and amine compound.

Hydrogen donors used in the preparation process of amine compounds of the invention by means of reductive amination reaction refer to a compound that can donate hydrogen by a thermal action or by a catalyst action, and the kind of such hydrogen-donating compound is not particularly limited. Examples of preferable hydrogen-donating compounds include, but are not limited to, methanol, ethanol, 1-propanol, 2-propanol, 1-butanol, sec-butyl alcohol, n-pentyl alcohol, cyclopentyl alcohol, n-hexyl alcohol, cyclohexyl alcohol, benzyl alcohol, formic acid, HCOOK, HCOONa, HCOOLi and HCOONH$_4$. These may be used alone, or a combination of a plurality of these may be used. From the viewpoints of reactivity and economic efficiency, hydrogen-donating compounds are preferably formic acid or formate.

The amount of a hydrogen-donating compound used may be 1-30 equivalents relative to the carbonyl compound; from the viewpoints of reactivity and economic efficiency, it is preferably 1-10 equivalents.

When formate such as HCOOK, HCOONa, HCOOLi and HCOONH$_4$ is used as a hydrogen donator, a phase-transfer catalyst may be added to carry out the reaction if necessary. The phase-transfer catalyst that can be used may be any salts having a long-chain alkyl ammonium cation; from the viewpoints of reactivity and economic efficiency, it is preferably a tetrabutylammonium salt. In many cases, an effect of increased reaction rate is observed by the addition of a phase-transfer catalyst. The amount of the phase-transfer catalyst added is generally between 0.001-10 molar equivalents relative to the carbonyl compound; from the viewpoints of reactivity and economic efficiency, it is preferably 0.01-0.1 molar equivalents.

With the present invention, one-pot preparation of amine compounds is possible by generating an imine compound or enamine compound in a reaction system using a carbonyl compound and amine compound as starting materials to carry out direct reductive amination reaction.

The carbonyl compound used as a raw material for imine compound or enamine compound is, for example, those represented by general formula (9); however, it is not necessarily limited thereto. Regarding general formula (9), R$^5$ and R$^6$ may be mutually the same or different, and denote a hydrogen atom, or a hydrocarbyl group, aryl group, heterocyclyl group, carboxyl group, ester group or acyl group in which one or more hydrogen atoms may be substituted by any substituents.

Specific examples of R$^5$ and R$^6$ include, but are not limited to, alkyl groups such as methyl, ethyl, propyl, butyl, pentyl, hexyl, heptyl, etc., fluoroalkyl group such as trifluoroalkyl group, etc., cycloalkyl groups such as cyclopropyl, cyclobutyl, cyclopentyl, cyclohexyl, etc., unsaturated hydrocarbons such as vinyl and allyl, aromatic mono- or polycyclic groups such as phenyl, 1-naphthyl, 2-naphthyl, anthryl, phenanthryl, indenyl, etc., hetero mono- or polycyclic groups such as thienyl, furyl, pyranyl, xanthenyl, pyridyl, pyrrolyl, imidazolinyl, indolyl, carbazoyl, phenanthrolinyl, etc., ferrocenyl group, carboxylic acid, ester groups such as methoxycarbonyl group, ethoxycarbonyl group, etc., acyl groups such as formyl group, acetyl group, benzoyl group, etc.

As substituents, any groups may be contained, including, but not limited to, hydrocarbon groups such as alkyl, alkenyl, cycloalkyl, cycloalkenyl, etc., fluoroalkyl groups, halogen atom, hydroxyl group, acyl groups, oxygen-containing groups such as alkoxy group, carboxyl group, ester group, etc., amino group, amide group, sulfonyl group, sulfenyl group, sulfo group, thiol group, silyl group, nitro group, cyano group, and etc. Furthermore, $R^5$ and $R^6$ may be bound to form a ring, and examples of such cases include, but are not limited to, saturated and unsaturated alicyclic groups that give cyclic ketones such as cyclopentanone, cyclohexanone, cycloheptanone, cyclopentenone, cyclohexenone, cycloheptenone, as well as saturated and unsaturated alicyclic groups that have a substituent having, at its respective carbon, an alkyl group, an aryl group, an unsaturated alkyl group, or a linear or cyclic hydrocarbon group comprising a hetero atom.

The amine compound as a raw material of the present invention is, for example those represented by general formula (10), but is not necessarily limited thereto. Regarding general formula (10), $R^7$ and $R^8$ may be the same or different each other, and they are a hydrogen atom, a hydrocarbyl group in which one or more hydrogen atoms may be substituted by any substituents, or a heterocyclyl group in which one or more hydrogen atoms may be substituted by any substituents.

Specific examples of $R^7$ and $R^8$ include, but are not limited to, alkyl groups such as methyl, ethyl, propyl, butyl, pentyl, hexyl, heptyl, etc., cycloalkyl groups such as cyclopropyl, cyclobutyl, cyclopentyl, cyclohexyl, etc., unsaturated hydrocarbons such as vinyl and allyl, aromatic mono- or polycyclic groups such as phenyl, 1-naphthyl, 2-naphthyl, anthryl, phenanthryl, indenyl, etc., hetero mono- or polycyclic groups such as thienyl, furyl, pyranyl, xanthenyl, pyridyl, pyrrolyl, imidazolinyl, indolyl, carbazoyl, phenanthrolinyl, etc., and ferrocenyl group, etc.

As substituents, any groups may be contained, including hydrocarbon groups such as alkyl, alkenyl, cycloalkyl, cycloalkenyl, etc., fluoroalkyl group, halogen atom, hydroxyl group, acyl groups, oxygen-containing groups such as alkoxy group, carboxyl group, ester group, etc., and amido group, amide group, sulfonyl group, sulfenyl group, sulfo group, thiol group, silyl group, nitro group, cyano group, etc. Furthermore, $R^7$ and $R^8$ may be bound to form a ring, and examples of such cases include, but are not limited to, saturated and unsaturated alicyclic groups that give cyclic ketones such as pyrrolidine, piperidine, azepane, pyrrole, tetrahydropyridine, tetrahydroazepine, etc., as well as saturated and unsaturated alicyclic groups that have a substituent having, at its respective carbon, an alkyl group, an aryl group, an unsaturated alkyl group, or a linear or cyclic hydrocarbon group comprising a hetero atom.

The amount of an amine compound used may be generally between 1-30 equivalents relative to the carbonyl compound; from the viewpoints of reactivity and economic efficiency, it is preferably 1-10 equivalents. When a gas such as ammonia is used as an amine compound, the gas may be used as is, or may be dissolved in an ammonia water or solvent, etc., or may be used as an ammonium salt.

A ruthenium, rhodium or iridium complex of general formula (5) used in the present invention may be prepared by mixing an organometallic compound of general formula (7):
[Chem. 17]

$$(ArMX_2)_m \qquad (7)$$

with a nitrogen-containing ligand of general formula (8):

[Chem. 18]

(8)

For example, a catalyst comprising the organometallic compound of general formula (5) of the present invention may be obtained as follows: under an inert gas atmosphere, an organometallic compound of general formula (7), a nitrogen-containing ligand of general formula (8), and a base are mixed in a halogen solvent, and stirred at room temperature; the resulting solution is washed with water and the solvent is distilled away, then dried under reduced pressure.

An amount of catalyst used can be expressed by a molar ratio S/C of a carbonyl compound relative to a ruthenium, rhodium or iridium catalyst (S denotes number of moles of carbonyl compound and C denotes number of moles of catalyst). In this case, possible levels of S/C vary significantly depending on the structure of a substrate, kind of a catalyst, and kind of a hydrogen donator, etc.; practically, an S/C value should desirably be set at approximately 100-20000.

In the present invention, considering the physical and chemical properties of imine compounds or enamine compounds, carbonyl compounds, amine compounds and hydrogen-donating compounds, a reaction solvent may appropriately be used. A protic solvent, non-protic solvent, ionic liquid, and water may be used alone, or a combination of a plurality of these may be used.

Reaction temperature may be any temperature suitable for starting materials, and it can be easily understood by those skilled in the art. From the viewpoint of economic efficiency, reaction can be carried out preferably at approximately from −20° C. to 100° C., and more preferably from 20° C. to 60° C. Reaction time may vary depending on reaction conditions such as substrate concentration, temperature and pressure, etc.; reaction will be completed within several minutes to 100 hours.

Purification of amine compounds generated may be performed using a publicly known method such as acid-base extraction, column chromatography, distillation, and re-crystallization, or an appropriate combination thereof.

Under the presence of an organometallic compound of general formula (7) and an organic compound of general formula (8), it is possible to synthesize an amine compound by reacting a carbonyl compound, an amine compound and a hydrogen-donating organic or inorganic compound.

Hereinafter, examples are shown and the present invention is described in more detail; however, the present invention is not limited to these examples. Reactions described in each of the examples and comparative examples below were performed under the atmosphere of inert gas such as argon and nitrogen. As a carbonyl compound and amine compound, commercially-available reagents were used as they were. Identification of ligand complexes and reaction products was performed using a nuclear magnetic resonance (NMR) apparatus, with tetramethylsilane (TMS) as the internal standard substance with its signal as δ=0 (δ denotes chemical shift). Conversion rates to amine compounds and reaction yields of amine compounds were determined by gas chromatography (GC) of crude products or by NMR of the crude products, and calculated using integral values of starting materials, end products and by-products. Conversion rates to amine compounds were calculated as [(sum of integral values of end products and by-products)/(sum of each integral values of starting materials, end products and by-products)]×100, and reaction yields of amine compounds were calculated as [(integral value of end product)/(sum of each integral values of starting materials, end products and by-products)]×100. Isolated yield were defined as yield of actually isolated reaction products, and calculated as (number of moles of isolated reaction product/number of moles of starting compound)×100. As a NMR apparatus, JNM-ECX-400P (JEOL Ltd.) was used; as a GC apparatus, GC-17A (Shimadzu Corporation) was used and as a separation column, capillary column TC-1 (column length 30 m, I.D. 0.32 mm, film thickness 0.25 μm, GL Science Inc.). FIG. 1 shows organometallic complexes that can be used as the examples.

Example 1

Synthesis of Ruthenium Complex, Rhodium Complex and Iridium Complex

Synthesis of RuCl(2-picolinamide) (p-cymene) complex (Ru-1)

200 mg (0.327 mmol) of [RuCl$_2$(p-cymene)]$_2$ (MW: 612.4), 79.7 mg (0.653 mmol) of 2-picolinamide (MW: 122.12) and 44.4 mg (0.653 mmol) of EtONa (MW: 68.05) were introduced in a 20-mL Schlenk tube and subjected to argon-gas replacement. 7 mL of dehydrated methanol was added and the mixture was stirred at room temperature for 24 hr. The reactant solution was evaporated to dryness, to which 20 mL of acetone was added and stirred, then the resulting solution was transferred to another 50-mL Schlenk tube with a filtration operation. After acetone was distilled away, the crystal was suspended and washed twice with 7 mL of acetone, and dried under reduced pressure to give 90 mg of yellow ocher crystal (35% isolated yield).

$^1$H-NMR (400 MHz, CDCl$_3$, δ/ppm): 1.16 (d, J=6.9 Hz, 3H), 1.19 (d, J=6.9 Hz, 3H), 2.25 (s, 3H), 2.70-2.85 (m, 1H), 5.37 (d, J=5.5 Hz, 1H), 5.45 (d, J=5.5 Hz, 1H), 5.52 (d, J=5.5 Hz, 1H), 5.63 (d, J=5.5 Hz, 1H), 7.40-7.58 (m, 1H), 7.89-7.98 (m, 1H), 8.00 (d, J=7.8 Hz, 1H), 9.01 (d, J=5.5 Hz, 1H)

$^{13}$C-NMR (100 MHz, CDCl$_3$, δ/ppm): 18.8, 22.0, 22.5, 31.0, 80.9, 83.0, 83.6, 84.5, 100.1, 102.3, 125.3, 126.32, 138.5, 153.0, 155.0, 171.0

Example 2

Synthesis of Cp*RhCl(2-picolinamide) complex (Rh-1)

150 mg (0.243 mmol) of [Cp*RhCl$_2$]$_2$ (MW: 618.08) and 59 mg (0.485 mmol) of 2-picolinamide (MW: 122.12) were introduced in a 20-mL Schlenk tube and subjected to argon-gas replacement. 5 mL of dehydrated methylene chloride and 71 μL (0.509 mmol) of triethylamine (MW: 101.19) were added and the mixture was stirred at room temperature for 1 hr. Then 10 mL of methylene chloride was added, the resulting solution was washed twice with a small amount of water, and solvent in the organic layer was distilled away, and it was dried under reduced pressure to give 164 mg of orange powder crystal (86% isolated yield).

$^1$H-NMR (400 MHz, CDCl$_3$, δ/ppm): 1.72 (s, 15H), 5.45 (brs, 1H), 7.48-7.55 (m, 1H), 7.88-7.96 (m, 1H), 8.06 (d, J=7.8 Hz, 1H), 8.60 (d, J=5.0 Hz, 1H)

$^{13}$C-NMR (100 MHz, CDCl$_3$, δ/ppm): 9.1, 94.0, 94.1, 125.6, 126.9, 138.8, 149.8, 155.6, 155.7, 170.6

Example 3

Synthesis of Cp*RhCl(8-quinolinolate) complex (Rh-2)

100 mg (0.162 mmol) of [Cp*RhCl$_2$]$_2$ (MW: 618.08) and 47 mg (0.324 mmol) of 8-quinolinol (MW: 145.16) were introduced in a 20-mL Schlenk tube and subjected to argon-gas replacement. 4 mL of dehydrated methylene chloride and 45 μL (0.324 mmol) of triethylamine (MW: 101.19) were added and the mixture was stirred at room temperature for 1 hr. This solution was washed twice with 5 mL of water and solvent in the organic layer was distilled away, and it was dried under reduced pressure to give 132 mg of orange powder crystal (98% isolated yield).

$^1$H-NMR (400 MHz, CDCl$_3$, δ/ppm): 1.73 (s, 15H), 6.79 (d, J=7.3 Hz, 1H), 7.02 (dd, J=7.8, 0.9 Hz, 1H), 7.30-7.38 (m, 2H), 8.07 (dd, J=8.2, 0.9 Hz, 1H), 8.55 (dd, J=4.6, 0.9 Hz, 1H)

$^{13}$C-NMR (100 MHz, CDCl$_3$, δ/ppm): 8.9, 93.1, 93.2, 109.8, 115.1, 121.8, 130.5, 130.8, 137.6, 145.5, 145.9, 167.0

Example 4

Synthesis of Cp*RhCl(N-benzyl-2-pyridinecarboxamide) complex (Rh-3)

155 mg (0.251 mmol) of [Cp*RhCl$_2$]$_2$ (MW: 618.08) and 107 mg (0.502 mmol) of N-benzyl-2-pyridinecarboxamide (MW: 212.25) were introduced in a 20-mL Schlenk tube and subjected to argon-gas replacement. 6 mL of dehydrated methylene chloride (Kanto Chemical Co., Inc.) and 70 μL (0.502 mmol) of triethylamine (MW: 101.19) were added and the mixture was stirred at room temperature for 20 hr. After this solution was washed three times with 6 mL of water, the methylene chloride was distilled away. Then, 6 mL of ethyl acetate was added and the mixture was stirred at room temperature for 1 hr, and a crystal was collected by filtration, washed with a small amount of ethyl acetate, dried under reduced pressure to give 138 mg of orange powder crystal (57% isolated yield).

$^1$H-NMR (400 MHz, CDCl$_3$, δ/ppm): 1.59 (s, 15H), 4.93 (d, J=15.1 Hz, 1H), 5.03 (d, J=15.1 Hz, 1H), 7.16 (t, J=7.3 Hz, 1H), 7.23-7.32 (m, 2H), 7.44-7.55 (m, 3H), 7.91 (td, J=7.8, 1.4 Hz, 1H), 8.10 (dd, J=8.7, 0.9 Hz, 1H), 8.61 (d, J=5.0 Hz, 1H)

$^{13}$C-NMR (100 MHz, CDCl$_3$, δ/ppm): 9.1, 54.7, 94.5, 94.6, 125.7, 125.9, 126.4, 127.8, 127.9, 138.6, 141.4, 149.1, 156.3, 169.4

Example 5

Synthesis of Cp*RhCl(N-(4'-methoxyphenyl)-2-pyridinecarboxamide) complex (Rh-4)

200 mg (0.324 mmol) of [Cp*RhCl$_2$]$_2$ (MW: 618.08) and 148 mg (0.647 mmol) of N-(4'-methoxyphenyl)-2-pyridinecarboxamide (MW: 228.25) were introduced in a 20-mL Schlenk tube and subjected to argon-gas replacement. 6 mL of dehydrated methylene chloride (Kanto Chemical Co., Inc.) and 90.3 μL (0.647 mmol) of triethylamine (MW: 101.19) were added and the mixture was stirred at room temperature for 16 hr. After this solution was washed three times with 6 mL of water, the methylene chloride was distilled away. Then, 20 mL of ethyl acetate was added and the mixture was stirred at room temperature for 1 hr, and a crystal was collected by filtration, washed with a small amount of ethyl acetate, dried under reduced pressure to give 282 mg of orange powder crystal (87% isolated yield).

$^1$H-NMR (400 MHz, CDCl$_3$, δ/ppm): 1.42 (s, 15H), 3.82 (s, 3H), 6.85-6.93 (m, 2H), 7.51 (ddd, J=7.3, 5.5, 1.8 Hz, 1H), 7.66-7.76 (m, 2H), 7.93 (td, J=7.8, 1.4 Hz, 1H), 8.14 (dd, J=7.8, 0.9, 1H), 8.62 (d, J=5.9 Hz, 1H)

$^{13}$C-NMR (100 MHz, CDCl$_3$, δ/ppm): 8.6, 55.5, 94.5, 94.6, 113.3, 125.9, 126.7, 127.9, 138.7, 141.4, 149.5, 156.1, 156.7, 166.7

Example 6

Synthesis of Cp*IrCl(2-picolinamide) complex (Ir-1)

100 mg (0.126 mmol) of [Cp*IrCl$_2$]$_2$ (MW: 796.67) and 30.7 mg (0.251 mmol) of 2-picolinamide (MW: 122.12) were introduced in a 20-mL Schlenk tube and subjected to argon-gas replacement. 4 mL of dehydrated methylene chloride and 35 μL (0.25 mmol) of triethylamine (MW: 101.19) were added and the mixture was stirred at room temperature for 1 hr. Then 10 mL of methylene chloride was added, the resulting solution was washed twice with a small amount of water, and solvent in the organic layer was distilled away, then it was dried under reduced pressure to give 103 mg of orange powder crystal (85% isolated yield).

$^1$H-NMR (400 MHz, CDCl$_3$, δ/ppm): 1.73 (s, 15H), 6.02 (brs, 1H), 7.47 (ddd, J=7.3, 5.5, 0.9 Hz, 1H), 7.92 (ddd, J=7.8, 7.3, 1.4 Hz, 1H), 8.08 (dd, J=7.8, 0.9 Hz, 1H), 8.56 (dd, J=5.0, 1.4 Hz, 1H)

$^{13}$C-NMR (100 MHz, CDCl$_3$, δ/ppm): 9.0, 86.0, 126.0, 127.4, 138.7, 150.1, 154.5, 172.4

Example 7

Synthesis of Cp*IrCl(8-quinolinolate) complex (Ir-2)

700 mg (0.879 mmol) of [Cp*IrCl$_2$]$_2$ (MW: 796.67) and 255 mg (1.757 mmol) of 8-quinolinol (MW: 145.16) were introduced in a 50-mL Schlenk tube and subjected to argon-gas replacement. 30 mL of dehydrated methylene chloride and 245 μL (1.757 mmol) of triethylamine (MW: 101.19) were added and the mixture was stirred at room temperature for 1 hr. This solution was washed twice with 15 mL of water and solvent in the organic layer was distilled away, and it was dried under reduced pressure to give 0.872 g of yellow powder crystal (98% isolated yield).

$^1$H-NMR (400 MHz, CDCl$_3$, δ/ppm): 1.72 (s, 15H), 6.78 (d, J=7.8 Hz, 1H), 7.00 (d, J=8.2 Hz, 1H), 7.31 (dd, J=8.2, 5.0, 1H), 7.36 (t, J=8.2 Hz, 1H), 8.03 (dd, J=8.2, 0.9 Hz, 1H), 8.54 (dd, J=5.0, 0.9 Hz, 1H)

$^{13}$C-NMR (100 MHz, CDCl$_3$, δ/ppm): 8.8, 84.8, 110.9, 115.6, 121.9, 130.7, 131.0, 137.7, 145.8, 146.0, 169.0

Example 8

Synthesis of Cp*IrCl(7-propylquinolinolate) complex (Ir-3)

100 mg (0.126 mmol) of [Cp*IrCl$_2$]$_2$ (MW: 796.67) was introduced in a 20-mL Schlenk tube and subjected to argon-gas replacement. 4 mL of dehydrated methylene chloride, 43 μL (0.25 mmol) of 7-propylquinolinol (MW: 187.24) and 35 μL (0.25 mmol) of triethylamine (MW: 101.19) were added and the mixture was stirred at room temperature for 1 hr. This solution was washed twice with 5 mL of water and solvent in the organic layer was distilled away, and it was dried under reduced pressure to give 135 mg of yellow powder crystal (98% isolated yield).

$^1$H-NMR (400 MHz, CDCl$_3$, δ/ppm): 0.98 (t, J=7.3 Hz, 3H), 1.71 (s, 15H), 1.65-1.83 (m, 2H), 2.58-2.70 (m, 1H), 3.10-3.24 (m, 1H), 6.74 (d, J=7.8 Hz, 1H), 7.23 (dd, J=8.2, 5.0 Hz, 1H), 7.29 (d, J=7.8 Hz, 1H), 7.97 (dd, J=8.2, 0.9 Hz, 1H), 8.49 (dd, J=5.0, 0.9 Hz, 1H)

$^{13}$C-NMR (100 MHz, CDCl$_3$, δ/ppm): 8.8, 14.2, 23.2, 32.1, 84.6, 110.2, 120.8, 129.3, 129.9, 131.7, 137.5, 144.9, 146.0, 166.5

Example 9

Synthesis of Cp*IrCl (3,5-dimethylpicolinamide) complex (Ir-4)

200 mg (0.251 mmol) of [Cp*IrCl$_2$]$_2$ (MW: 796.67) and 75.4 mg (0.502 mmol) of 3,5-dimethylpicolinamide (MW: 150.18) were introduced in a 20-mL Schlenk tube and subjected to argon-gas replacement. 6 mL of dehydrated methylene chloride (Kanto Chemical Co., Inc.) and 70 μL (0.502 mmol) of triethylamine (MW: 101.19) were added and the mixture was stirred at room temperature for 16 hr. After this solution was washed three times with 6 mL of water, the methylene chloride was distilled away. Then, 20 ml of dehydrated diisopropyl ether (Kanto Chemical Co., Inc.) was added and the mixture was stirred at room temperature for 1 hr, and a crystal was collected by filtration, washed with a small amount of dehydrated diisopropyl ether, dried under reduced pressure to give 248 mg of orange powder crystal (96% isolated yield).

$^1$H-NMR (400 MHz, CDCl$_3$, δ/ppm): 1.71 (s, 15H), 2.39 (s, 3H), 2.75 (s, 3H), 5.79 (brs, 1H), 7.43 (s, 1H), 8.27 (s, 1H)

$^{13}$C-NMR (100 MHz, CDCl$_3$, δ/ppm): 8.9, 18.0, 18.6, 85.8, 136.5, 138.4, 142.9, 148.0, 149.0, 174.1

Example 10

Synthesis of Cp*IrCl(isoquinoline-3-pyridinecarboxamide) complex (Ir-5)

200 mg (0.251 mmol) of [Cp*IrCl$_2$]$_2$ (MW: 796.67) and 86.5 mg (0.502 mmol) of isoquinoline-3-pyridinecarboxamide (MW: 172.18) were introduced in a 20-mL Schlenk tube and subjected to argon-gas replacement. 6 mL of dehydrated methylene chloride (Kanto Chemical Co., Inc.) and 70 μL (0.502 mmol) of triethylamine (MW: 101.19) were added and the mixture was stirred at room temperature for 16 hr. After this solution was washed three times with 6 mL of water, the methylene chloride was distilled away. Then, 20 ml of dehydrated diisopropyl ether (Kanto Chemical Co., Inc.) was added and the mixture was stirred at room temperature for 1 hr, and a crystal was collected by filtration, washed with a small amount of dehydrated diisopropyl ether, dried under reduced pressure to give 251 mg of yellow powder crystal (94% isolated yield).

$^1$H-NMR (400 MHz, CDCl$_3$, δ/ppm): 1.75 (s, 15H), 5.86 (brs, 1H), 7.76 (ddd, J=8.2, 6.9, 0.9 Hz, 1H), 7.83 (ddd, J=8.2, 6.9, 1.4 Hz, 1H), 8.01 (d, J=8.2 Hz, 1H), 8.05 (d, J=8.2 Hz, 1H), 8.47 (s, 1H), 9.22 (s, 1H)

$^{13}$C-NMR (100 MHz, CDCl$_3$, δ/ppm): 8.9, 86.0, 123.9, 127.5, 128.0, 129.3, 130.4, 132.8, 136.1, 146.9, 153.6, 172.6

Example 11

Synthesis of Cp*IrCl(N-benzyl-2-pyridinecarboxamide) complex (Ir-6)

200 mg (0.251 mmol) of [Cp*IrCl$_2$]$_2$ (MW: 796.67) and 107 mg (0.502 mmol) of N-benzyl-2-pyridinecarboxamide (MW: 212.25) were introduced in a 20-mL Schlenk tube and subjected to argon-gas replacement. 6 mL of dehydrated methylene chloride (Kanto Chemical Co., Inc.) and 70 μL (0.502 mmol) of triethylamine (MW: 101.19) were added and the mixture was stirred at room temperature for 16 hr. After this solution was washed three times with 6 mL of water, the methylene chloride was distilled away. Then, 5 ml of ethyl acetate was added and the mixture was stirred at room temperature for 1 hr, and a crystal was collected by filtration, washed with a small amount of ethyl acetate, dried under reduced pressure to give 135 mg of yellow powder crystal (47% isolated yield).

$^1$H-NMR (400 MHz, CDCl$_3$, δ/ppm): 1.58 (s, 15H), 4.90 (d, J=15.1 Hz, 1H), 5.13 (d, J=15.1 Hz, 1H), 7.16 (t, J=7.3 Hz, 1H), 7.22-7.35 (m, 2H), 7.40-7.50 (m, 3H), 7.90 (t, J=7.8 Hz, 1H), 8.11 (d, J=7.8 Hz, 1H), 8.55 (d, J=6.0 Hz, 1H)

$^{13}$C-NMR (100 MHz, CDCl$_3$, δ/ppm): 9.0, 55.2, 86.6, 125.9, 126.0, 126.9, 127.6, 127.8, 138.4, 140.6, 149.1, 155.3, 171.3

Example 12

Synthesis of Cp*IrCl(N-(4'-methoxyphenyl)-2-pyridinecarboxamide) complex (Ir-7)

200 mg (0.251 mmol) of [Cp*IrCl$_2$]$_2$ (MW: 796.67) and 115 mg (0.502 mmol) of N-(4'-methoxyphenyl)-2-pyridinecarboxamide (MW: 228.25) were introduced in a 20-mL Schlenk tube and subjected to argon-gas replacement. 6 mL of dehydrated methylene chloride (Kanto Chemical Co., Inc.) and 70 μL (0.502 mmol) of triethylamine (MW: 101.19) were added and the mixture was stirred at room temperature for 16 hr. After this solution was washed three times with 6 mL of water, the methylene chloride was distilled away. Then, 15 ml of dehydrated diisopropyl ether (Kanto Chemical Co., Inc.) was added and the mixture was stirred at room temperature for 1 hr, and a crystal was collected by filtration, washed with a small amount of dehydrated diisopropyl ether, dried under reduced pressure to give 277 mg of yellow powder crystal (94% isolated yield).

$^1$H-NMR (400 MHz, CDCl$_3$, δ/ppm): 1.42 (s, 15H), 3.81 (s, 3H), 6.84-6.92 (m, 2H), 7.48 (ddd, J=7.3, 5.5, 1.8 Hz, 1H), 7.55-7.64 (m, 2H), 7.91 (td, J=7.8, 1.4 Hz, 1H), 8.15 (dd, J=7.8, 0.9, 1H), 8.56 (d, J=5.5 Hz, 1H)

$^{13}$C-NMR (100 MHz, CDCl$_3$, δ/ppm): 8.5, 55.5, 86.5, 113.3, 126.3, 127.2, 127.6, 138.5, 141.3, 149.5, 155.8, 156.3, 168.6

Example 13

Synthesis of Cp*IrCl(Pyrazinamide) complex (Ir-8)

200 mg (0.251 mmol) of [Cp*IrCl$_2$]$_2$ (MW: 796.67) and 61.8 mg (0.502 mmol) of Pyrazinamide (MW: 123.11) were introduced in a 20-mL Schlenk tube and subjected to argon-gas replacement. 6 mL of dehydrated methylene chloride (Kanto Chemical Co., Inc.) and 70 μL (0.502 mmol) of triethylamine (MW: 101.19) were added and the mixture was stirred at room temperature for 16 hr. After 12 ml of methylene chloride was added to the solution and this solution was washed twice with 2 ml of water, the methylene chloride was distilled away. Then, 18 ml of dehydrated diisopropyl ether (Kanto Chemical Co., Inc.) and 2 ml of dehydrated methylene chloride were added and the mixture was stirred at room temperature for 1 hr, and a crystal was collected by filtration, washed with a small amount of dehydrated diisopropyl ether, dried under reduced pressure to give 176 mg of brown powder crystal (72% isolated yield).

$^1$H-NMR (400 MHz, CDCl$_3$, δ/ppm): 1.75 (s, 15H), 5.87 (brs, 1H), 8.51 (dd, J=3.2, 0.9, 1H), 8.75 (brs, 1H), 9.27 (s, 1H)

$^{13}$C-NMR (100 MHz, CDCl$_3$, δ/ppm): 9.0, 87.0, 143.3, 148.4, 148.4, 148.4, 171.1

Comparative Example 1

Synthesis of N-benzyl-2-penthylamine by reductive amination reaction of 2-pentanone and benzylamine Under an argon-gas atmosphere, 532 μL (5.0 mmol) of 2-pentanone (MW: 86.13), 572 μL (5.25 mmol) of benzylamine (MW: 107.15), and 0.5 mL of dehydrated ethyl acetate (Kanto Chemical Co., Inc.) were added to a 20-mL Schlenk tube and ice-cooled. 566 μL (15.0 mmol) of formic acid (MW: 46.03) was added and stirred for approximately 5 min, then the ice bath was removed, and 1.99 mg (0.0025 mmol) of [Cp*IrCl$_2$]$_2$ (MW: 796.67) was added and stirred at 40° C. for 18 hr. After the reaction was completed, a saturated sodium hydrogen carbonate solution was added and stirred for approximately 5 min, then the product was extracted with ether. The organic phase was analyzed by GC to calculate the conversion rate and the reaction yield. As a result of the analysis, the conversion rate and the reaction yield were determined to be 9.7% and 1.6%, respectively.

Comparative Example 2

Synthesis of N-benzyl-2-penthylamine by reductive amination reaction of 2-pentanone and benzylamine A reaction was carried out with the same condition as that of Comparative example 1, except that 1.55 mg (0.0025 mmol) of [Cp*RhCl$_2$]$_2$ (MW: 618.08) was used as a catalyst. The conversion rate and the reaction yield were 56% and 52%, respectively.

Example 14

Synthesis of N-benzyl-2-penthylamine by reductive amination reaction of 2-pentanone and benzylamine Under an argon-gas atmosphere, 532 μL (5.0 mmol) of 2-pentanone (MW: 86.13), 572 μL (5.25 mmol) of benzylamine (MW: 107.15), and 0.5 mL of dehydrated ethyl acetate (Kanto Chemical Co., Inc.) were added to a 20-mL Schlenk tube and ice-cooled. 566 μL (15.0 mmol) of formic acid (MW: 46.03) was added and stirred for approximately 5 min, then the ice bath was removed, and as reaction examples 1-6, 0.0025 mmol of each of the complexes shown in FIG. 1 was added and stirred at 40° C. for 18 hr. After the reaction was completed, a saturated sodium hydrogen carbonate solution was added and stirred for approximately 5 min, then the product was extracted with ether. The organic phase was analyzed by GC to calculate conversion rates and the reaction yields. Results of the analysis were summarized in Table 1. Compared to Comparative examples 1 and 2, reactivities significantly increased when the inventive complexes of the same metals were used, suggesting the efficacy of the invention.

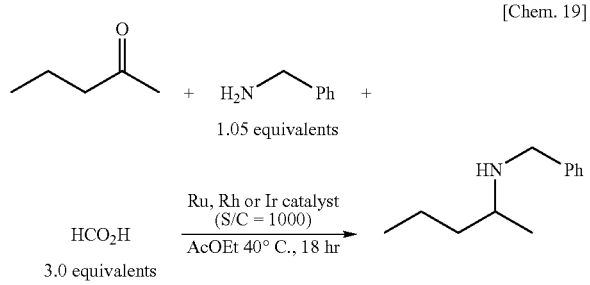

[Chem. 19]

TABLE 1

| Reaction example | Catalyst | Conversion rate (%) | Reaction yield (%) |
|---|---|---|---|
| 1 | Ru-1 | 35 | 26 |
| 2 | Ir-1 | 100 | 95 |
| 3 | Ir-2 | 100 | 96 |
| 4 | Ir-3 | 100 | 98 |
| 5 | Rh-1 | 93 | 88 |
| 6 | Rh-2 | 100 | 99 |

Example 15

Synthesis of cyclohexylbenzylamine by reductive amination reaction of cyclohexanone and benzylamine Under an argon-gas atmosphere, 520 μL (5.0 mmol) of cyclohexanone (MW: 98.15), 572 μL (5.25 mmol) of benzylamine (MW: 107.15), and 0.5 mL of dehydrated ethyl acetate (Kanto Chemical Co., Inc.) were added to a 20-mL Schlenk tube and ice-cooled. 566 μL (15.0 mmol) of formic acid (MW: 46.03) was added and stirred for approximately 5 min, then the ice bath was removed, and as reaction examples 7-10, 0.005 mmol of each of the complexes of Ir-1, Ir-2, Rh-1 and Rh-2 shown in FIG. 1 was added and stirred at 40° C. for 18 hr. After the reaction was completed, a saturated sodium hydrogen carbonate solution was added and stirred for approximately 5 min, then the product was extracted with ether. The organic phase was analyzed by GC to calculate conversion rates the reaction yields. Results of the analysis were summarized in Table 2.

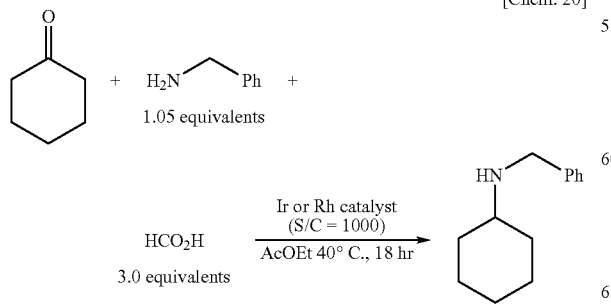

[Chem. 20]

TABLE 2

| Reaction example | Catalyst | Conversion rate (%) | Reaction yield (%) |
|---|---|---|---|
| 7 | Ir-1 | 96 | 92 |
| 8 | Ir-2 | 99 | 98 |
| 9 | Rh-1 | 98 | 95 |
| 10 | Rh-2 | 99 | 96 |

Example 16

Synthesis of DL-1-phenylethylamine 946 mg (15.0 mmol) of ammonium formate (MW: 63.06) was introduced in a 20-mL Schlenk tube and subjected to argon-gas replacement. To this, 5 mL of dehydrated methanol, 582 μL (5.0 mmol) of acetophenone (MW: 120.15), 582 μL (5.0 mmol) of acetic acid, and 12.1 mg (0.025 mmol, S/C=200) of the iridium catalyst Ir-1 (MW: 484.01) were added, and the mixture was stirred while heating at 60° C. for 5 hr. After distillation of the solvent, a saturated sodium hydrogen carbonate solution was added, then a product was extracted with methylene chloride, the organic layer was washed with water, and the product was dried with sodium sulfate. The drying agent was removed by filtration and the methylene chloride was distilled away to give a crude product DL-1-phenylethylamine. Its conversion rate was 100% based on NMR measurement, with 92.8% of DL-1-phenylethylamine, 0.4% of 1-phenylethanol, and 6.8% of other by-products.

Examples 17-24

A reaction was carried out with the same condition as that of Example 16, except that the kind of catalyst and S/C value were changed. Table 3 shows the catalyst, reaction condition and results of the catalytic reaction.

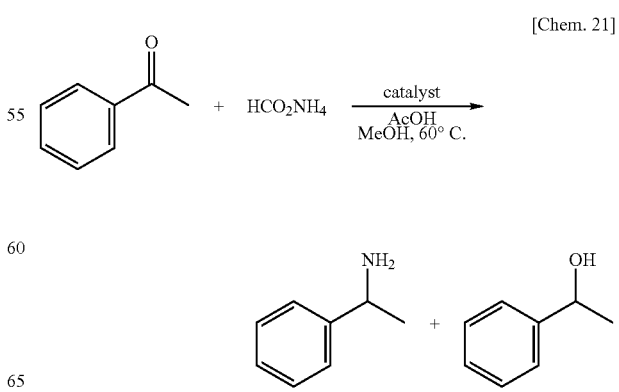

[Chem. 21]

TABLE 3

| Example No. | Catalyst | S/C | Time (h) | Conversion rate (%) | Ratio of each product (%) | | |
|---|---|---|---|---|---|---|---|
| | | | | | 1-phenyl ethylamine | 1-phenyl ethanol | others |
| 17 | Ir-2 | 100 | 5 | 93 | 83.7 | 0.4 | 15.9 |
| 18 | Ir-4 | 200 | 5 | 100 | 93.2 | 0.4 | 6.4 |
| 19 | Ir-5 | 200 | 5 | 100 | 92.9 | 0.6 | 6.5 |
| 20 | Ir-6 | 500 | 6 | 100 | 94.4 | 0.8 | 4.8 |
| 21 | Ir-7 | 500 | 5 | 100 | 96.9 | 0.4 | 2.7 |
| 22 | Ir-8 | 100 | 4 | 100 | 91.1 | 4.9 | 4.0 |
| 23 | Rh-3 | 100 | 4 | 78 | 91.9 | 4.8 | 3.3 |
| 24 | Rh-4 | 200 | 4 | 99 | 94.3 | 2.3 | 3.4 |

Example 25

Synthesis of DL-1-(4'-nitrophenyl)ethylamine 826 mg (5.0 mmol) of 4'-nitroacetophenone (MW: 165.15), 946 mg (15.0 mmol) of ammonium formate (MW: 63.06) and 5.90 mg (0.01 mmol, S/C=500) of the iridium catalyst Ir-7 (MW: 590.13) were introduced in a 20-mL Schlenk tube, and subjected to argon-gas replacement. To this, 5 mL of dehydrated methanol and 286 μL (5.0 mmol) of acetic acid were added and stirred while heating at 60° C. for 3 hr. After distillation of the solvent, a saturated sodium hydrogen carbonate solution was added, then a product was extracted with methylene chloride, the organic layer was washed with water, and the product was dried with sodium sulfate. The drying agent was removed by filtration and the methylene chloride was distilled away to give a crude product DL-1-(4'-nitrophenyl)ethylamine. Its conversion rate was 100% based on NMR measurement, with 96% of DL-1-(4'-nitrophenyl)ethylamine, 1% of 1-(4'-nitrophenyl)ethanol, and 3% of other by-products. Since no compound in which reduction of nitro groups occurred was generated, we confirmed that reductive amination reaction was carried out in a functional-group-selective manner.

$^1$H NMR data of DL-1-(4'-nitrophenyl)ethylamine:

$^1$H-NMR (400 MHz, CDCl$_3$, δ/ppm): 1.41 (d, J=6.9 Hz, 3H), 1.69 (brs, 2H), 4.26 (q, J=6.9 Hz, 1H), 7.50-7.58 (m, 2H), 8.15-8.24 (m, 2H)

Example 26

Synthesis of DL-1-(4'-cyanophenyl)ethylamine 726 mg (5.0 mmol) of 4'-cyanoacetophenone (MW: 145.16), 946 mg (15.0 mmol) of ammonium formate (MW: 63.06) and 5.90 mg (0.01 mmol, S/C=500) of the iridium catalyst Ir-7 (MW: 590.13) were introduced in a 20-mL Schlenk tube, and subjected to argon-gas replacement. To this, 5 mL of dehydrated methanol and 286 μL (5.0 mmol) of acetic acid were added and stirred while heating at 60° C. for 3 hr. After distillation of the solvent, a saturated sodium hydrogen carbonate solution was added, then a product was extracted with methylene chloride, the organic layer was washed with water, and the product was dried with sodium sulfate. The drying agent was removed by filtration and the methylene chloride was distilled away to give a crude product DL-1-(4'-cyanophenyl)ethylamine. Its conversion rate was 100% based on NMR measurement, with 95% of DL-1-(4'-cyanophenyl)ethylamine, 1% of 1-(4'-cyanophenyl)ethanol, and 4% of other by-products. Since no compound in which reduction of cyano groups occurred was generated, we confirmed that reductive amination reaction was carried out in a functional-group-selective manner.

$^1$H NMR data of DL-1-(4'-cyanophenyl)ethylamine:

$^1$H-NMR (400 MHz, CDCl$_3$, δ/ppm): 1.39 (d, J=6.4 Hz, 3H), 1.69 (brs, 2H), 4.20 (q, J=6.4 Hz, 1H), 7.45-7.52 (m, 2H), 7.58-7.66 (m, 2H)

Example 27

Synthesis of Dibenzylamine

Under an argon-gas atmosphere, 5 mL of dehydrated methanol, 505 μL (5.0 mmol) of benzaldehyde (MW: 106.12), 545 μL (5.0 mmol) of benzylamine (MW: 107.15), 566 μL (15.0 mmol) of formic acid (MW: 46.43), and 5.90 mg (0.01 mmol, S/C=500) of the iridium catalyst Ir-7 (MW: 590.13) were introduced in a 20-mL Schlenk tube, and the mixture was stirred while heating at 60° C. for 1.5 hr. After distillation of the solvent, a saturated sodium hydrogen carbonate solution was added, then a product was extracted with methylene chloride, the organic layer was washed with water, and the product was dried with sodium sulfate. The drying agent was removed by filtration and the methylene chloride was distilled away to give a crude product dibenzylamine. Its conversion rate was 100% based on NMR measurement, with 95% of dibenzylamine, 3% of tribenzylamine, and 2% of benzyl alcohol.

Examples 28

Synthesis of DL-2-phenylglycine 751 mg (5.0 mmol) of benzoyl formate (MW: 150.13), 946 mg (15.0 mmol) of ammonium formate (MW: 63.06), and 5.90 mg (0.01 mmol, S/C=500) of the iridium catalyst Ir-7 (MW: 590.13) were introduced in a 20-mL Schlenk tube and subjected to argon-gas replacement. 5 mL of dehydrated methanol was added and the mixture was stirred while heating at 60° C. for 1.5 hr. After distillation of the solvent, a crystal was collected by filtration, washed with methanol, dried under reduced pressure to give 718 mg of DL-2-phenylglycine (95% yield).

Industrial Applicability

As described above in detail, this invention provides a catalyst with superior practical utility for a process of preparing amine compounds by reductive amination reaction of carbonyl compounds and amine compounds, thereby enabling highly efficient production of amine compounds.

The invention claimed is:

1. An organometallic compound of general formula (4):

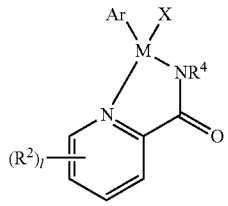
(4)

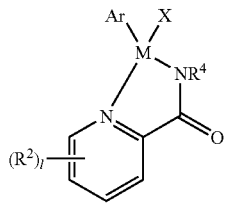
(4)

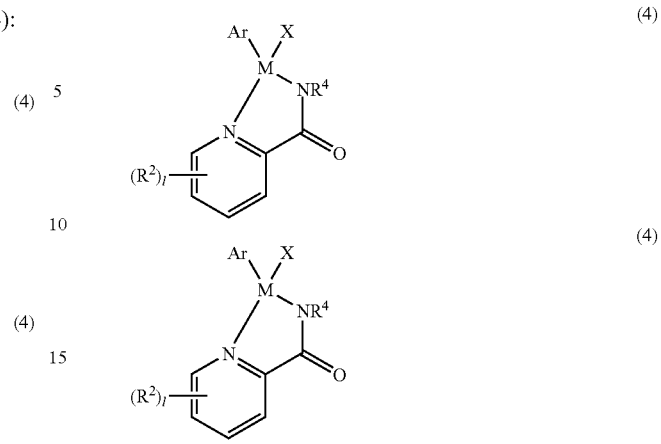

(wherein in general formula (4),

Ar is a cyclopentadienyl group or an aromatic compound in which one or more hydrogen atoms may be substituted by a substituent W, and W denotes a saturated or unsaturated C1-10 hydrocarbon group, an aryl group, a heterocyclyl group, an alkoxy group, a fluoroalkyl group, an acyl group, an ester group, a hydroxyl group, an amino group, an amide group, a carboxyl group, a sulfonyl group, a nitro group, a cyano group, a sulfenyl group, a sulfo group, a thiol group, a silyl group or a halogen group, M is ruthenium, rhodium, or iridium, X is a hydride group or an anionic group, each $R^2$ independently denotes a hydrogen atom, a halogen atom, a nitro group, a cyano group, a hydroxyl group, a sulfo group, a thiol group, a carboxyl group or the following groups in which one or more hydrogen atoms may be substituted by a substituent W: a C1-10 alkyl group, a cycloalkyl group, an aryl group, a heterocyclyl group, an alkenyl group, an alkynyl group, an alkoxy group, an ester group, a fluoroalkyl group, an acyl group, a sulfonyl group, an amino group, an amide group, a sulfenyl group, or a silyl group, $R^4$ denotes a hydrogen atom, a C1-10 alkyl group, a cycloalkyl group, an aryl group, a heterocyclyl group, an alkenyl group, an alkynyl group, an ester group, an acyl group, a sulfinyl group, a sulfonyl group, or a silyl group, in which one or more hydrogen atoms may be substituted by a substituent W, l denotes an integer from 0 to 4, wherein one or more of carbon atoms, which is(are) not bonded to $R^2$, in the pyridine ring structure may be replaced with a nitrogen atom, and wherein when l is 2 or more, 2 or more of $R^2$ may be linked to each other to form (a) ring(s)).

2. A catalyst for reductive amination reaction or for reduction or hydrogenation of an imine compound or enamine compound, comprising at least one organometallic compound of general formula (4):

(wherein in general formula (4),

Ar is a cyclopentadienyl group or an aromatic compound in which one or more hydrogen atoms may be substituted by a substituent W, and W denotes a saturated or unsaturated C1-10 hydrocarbon group, an aryl group, a heterocyclyl group, an alkoxy group, a fluoroalkyl group, an acyl group, an ester group, a hydroxyl group, an amino group, an amide group, a carboxyl group, a sulfonyl group, a nitro group, a cyano group, a sulfenyl group, a sulfo group, a thiol group, a silyl group or a halogen group, M is ruthenium, rhodium, or iridium, X is a hydride group or an anionic group, each $R^2$ independently denotes a hydrogen atom, a halogen atom, a nitro group, a cyano group, a hydroxyl group, a sulfo group, a thiol group, a carboxyl group or the following groups in which one or more hydrogen atoms may be substituted by a substituent W: a C1-10 alkyl group, a cycloalkyl group, an aryl group, a heterocyclyl group, an alkenyl group, an alkynyl group, an alkoxy group, an ester group, a fluoroalkyl group, an acyl group, a sulfonyl group, an amino group, an amide group, a sulfenyl group, or a silyl group, $R^4$ denotes a hydrogen atom, a C1-10 alkyl group, a cycloalkyl group, an aryl group, a heterocyclyl group, an alkenyl group, an alkynyl group, an ester group, an acyl group, a sulfinyl group, a sulfonyl group, or a silyl group, in which one or more hydrogen atoms may be substituted by a substituent W, l denotes an integer from 0 to 4, wherein one or more of carbon atoms, which is(are) not bonded to $R^2$, in the pyridine ring structure may be replaced with a nitrogen atom, and wherein when l is 2 or more, 2 or more of $R^2$ may be linked to each other to form (a) ring(s)).

3. The catalyst according to claim 2, wherein M in general formula (4) is rhodium or iridium.

4. A process for preparing an amine compound, wherein the amine compound is prepared by reacting a hydrogen-donating organic or inorganic compound with an imine compound or an enamine compound under the presence of the catalyst according to claim 2.

5. The process for preparing the amine compound according to claim 4, wherein the amine compound is prepared by the reaction of an imine compound or an enamine compound generated by mixing a carbonyl compound with an amine compound in a reaction system.

6. A process for preparing an organometallic compound of claim 3, wherein a carbonyl compound, an amine compound and a hydrogen-donating organic or inorganic compound are reacted under the presence of an organometallic compound of general formula (7):

$(ArMX_2)_m$       (7)

(wherein in general formula (7), Ar, M and X have the same meanings as defined in claim 3, and m denotes an integer of 2 or greater) and an organic compound of general formula (8'):

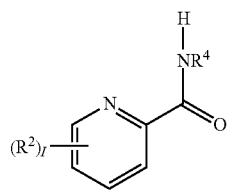

(8')

(wherein in general formula (8'), $R^2$, $R^4$, and 1 have the same meanings as defined in claim 3).

7. The process for preparing an organometallic compound according to claim 6, wherein the hydrogen-donating organic or inorganic compound is formic acid or formate.

8. A process for preparing an amine compound, wherein the amine compound is prepared by reacting a hydrogen-donating organic or inorganic compound with an imine compound or an enamine compound under the presence of the catalyst according to claim 3.

9. The process for preparing the amine compound according to claim 8, wherein the amine compound is prepared by the reaction of an imine compound or an enamine compound generated by mixing a carbonyl compound with an amine compound in a reaction system.

\* \* \* \* \*

UNITED STATES PATENT AND TRADEMARK OFFICE
CERTIFICATE OF CORRECTION

PATENT NO. : 8,481,735 B2
APPLICATION NO. : 12/722819
DATED : July 9, 2013
INVENTOR(S) : Masahito Watanabe et al.

It is certified that error appears in the above-identified patent and that said Letters Patent is hereby corrected as shown below:

In the Claims:

Claim 1, column 27, at line 2, should read:

1. An organometallic compound of general formula (4):

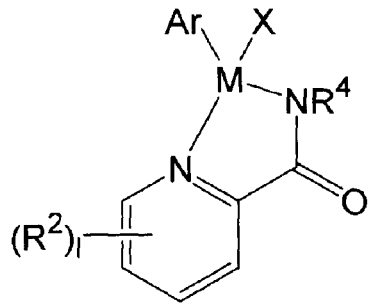

(4)

(wherein in general formula (4),

Ar is a cyclopentadienyl group or an aromatic compound in which one or more hydrogen atoms may be substituted by a substituent W, and W denotes a saturated or unsaturated C1-10 hydrocarbon group, an aryl group, a heterocyclyl group, an alkoxy group, a fluoroalkyl group, an acyl group, an ester group, a hydroxyl group, an amino group, an amide group, a carboxyl group, a sulfonyl group, a nitro group, a cyano group, a sulfenyl group, a sulfo group, a thiol group, a silyl group or a halogen group, M is ruthenium, rhodium, or iridium, Signed and Sealed this
Twelfth Day of November, 2013

Teresa Stanek Rea
*Deputy Director of the United States Patent and Trademark Office*

X is a hydride group or an anionic group, each R2 independently denotes a hydrogen atom, a halogen atom, a nitro group, a cyano group, a hydroxyl group, a sulfo group, a thiol group, a carboxyl group or the following groups in which one or more hydrogen atoms may be substituted by a substituent W: a C1-10 alkyl group, a cycloalkyl group, an aryl group, a heterocyclyl group, an alkenyl group, an alkynyl group, an alkoxy group, an ester group, a fluoroalkyl group, an acyl group, a sulfonyl group, an amino group, an amide group, a sulfenyl group, or a silyl group, $R^4$ denotes a hydrogen atom, a C1-10 alkyl group, a cycloalkyl group, an aryl group, a heterocyclyl group, an alkenyl group, an alkynyl group, an ester group, an acyl group, a sulfinyl group, a sulfonyl group, or a silyl group, in which one or more hydrogen atoms may be substituted by a substituent W, l denotes an integer from 0 to 4, wherein one or more of carbon atoms, which is(are) not bonded to $R^2$, in the pyridine ring structure may be replaced with a nitrogen atom, and wherein when l is 2 or more, 2 or more of $R^2$ may be linked to each other to form (a) ring(s)).

Claim 2, column 27, at line 64, should read:

2. A catalyst for reductive amination reaction or for reduction or hydrogenation of an imine compound or enamine compound, comprising at least one organometallic compound of general formula (4):

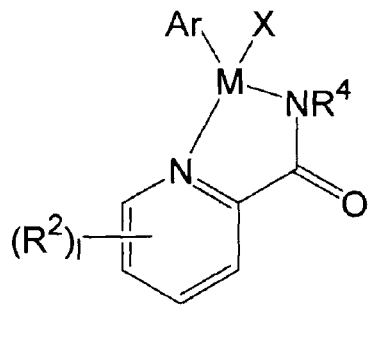

(4)

(wherein in general formula (4),

Ar is a cyclopentadienyl group or an aromatic compound in which one or more hydrogen atoms may be substituted by a substituent W, and W denotes a saturated or unsaturated C1-10 hydrocarbon group, an aryl group, a heterocyclyl group, an alkoxy group, a fluoroalkyl group, an acyl group, an ester group, a hydroxyl group, an amino group, an amide group, a carboxyl group, a sulfonyl group, a nitro group, a cyano group, a sulfenyl group, a sulfo group, a thiol group, a silyl group or a halogen group, M is ruthenium, rhodium, or iridium, X is a hydride group or an anionic group, each $R^2$ independently denotes a hydrogen atom, a halogen atom, a nitro group, a cyano group, a hydroxyl group, a sulfo group, a thiol group, a carboxyl group or the following groups in which one or more hydrogen atoms may be substituted by a substituent W: a C1-10 alkyl group, a cycloalkyl group, an aryl group, a heterocyclyl group, an alkenyl group, an alkynyl group, an alkoxy group, an ester group, a fluoroalkyl group, an acyl group, a sulfonyl group, an amino group, an amide group, a sulfenyl group, or a silyl group, $R^4$ denotes a hydrogen atom, a C1-10 alkyl group, a cycloalkyl group, an aryl group, a heterocyclyl group, an alkenyl group, an alkynyl group, an ester group, an acyl group, a sulfinyl group, a sulfonyl group, or a silyl group, in which one or more hydrogen atoms may be substituted by a substituent W, 1 denotes an integer from 0 to 4, wherein one or more of carbon atoms, which is(are) not bonded to $R^2$, in the pyridine ring structure may be replaced with a nitrogen atom, and wherein when 1 is 2 or more, 2 or more of $R^2$ may be linked to each other to form (a) ring(s)).

Claim 6, column 29, at line 1, should read:

6. A process for preparing an organometallic compound of claim 1, wherein a carbonyl compound, an amine compound and a hydrogen-donating organic or inorganic compound are reacted under the presence of an organometallic compound of general formula (7):

(7)

(wherein in general formula (7), Ar, M and X have the same meanings as defined in Claim 1, and m denotes an integer of 2 or greater) and an organic compound of general formula (8'):

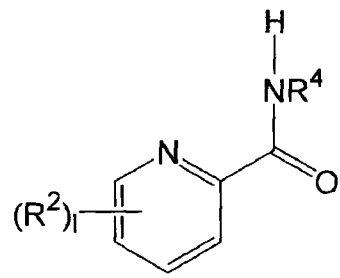

(8')

(wherein in general formula (8'), $R^2$, $R^4$, and l have the same meanings as defined in Claim 1).